United States Patent [19]
Primbsch et al.

[11] 4,379,409
[45] Apr. 12, 1983

[54] APPARATUS FOR PRODUCING ULTRASONIC WAVES IN A WORKPIECE

[75] Inventors: Erik Primbsch, Ahrensburg; Wolf Bickel, Bergisch Gladbach, both of Fed. Rep. of Germany

[73] Assignee: Krautkramer-Branson, Inc., Stratford, Conn.

[21] Appl. No.: 299,049

[22] Filed: Sep. 3, 1981

[30] Foreign Application Priority Data

Nov. 6, 1980 [DE] Fed. Rep. of Germany ....... 3041875

[51] Int. Cl.³ .................. G01N 9/24; G01N 29/00; G02B 5/14
[52] U.S. Cl. .................................. 73/643; 350/96.15
[58] Field of Search .............. 73/643; 350/358, 96.15, 350/96.16

[56] References Cited

U.S. PATENT DOCUMENTS

| | | | |
|---|---|---|---|
| 4,121,469 | 10/1978 | Kaule et al. | 73/643 |
| 4,121,470 | 10/1978 | Kaule | 73/643 |
| 4,128,759 | 12/1978 | Hunt et al. | 350/96.15 X |
| 4,144,767 | 3/1979 | Kaule et al. | 73/643 |
| 4,169,662 | 10/1979 | Kaule et al. | 181/142 X |
| 4,182,935 | 1/1980 | Chown | 350/96.15 X |
| 4,246,793 | 1/1981 | Fairand et al. | 73/643 x |
| 4,296,319 | 10/1981 | Franks et al. | 350/96.15 X |

OTHER PUBLICATIONS

Laser Excitation of Microwave Sound in Solids; by Cachier Journal of Acoustical Society of America, vol. 49, No. 3, part 3, published in 1971, pp. 974–978.

*Primary Examiner*—Anthony V. Ciarlante
*Assistant Examiner*—David V. Carlson
*Attorney, Agent, or Firm*—Ervin B. Steinberg; Philip J. Feig

[57] ABSTRACT

Laser light for producing acoustic waves in a specimen to be examined is carried to the specimen from a single laser by a plurality of fiber optic cables. The fiber optic cables have different path lengths to cause a specific time delay between adjacent fiber optic cables to focus and steer the sonic waves in a desired direction.

4 Claims, 5 Drawing Figures

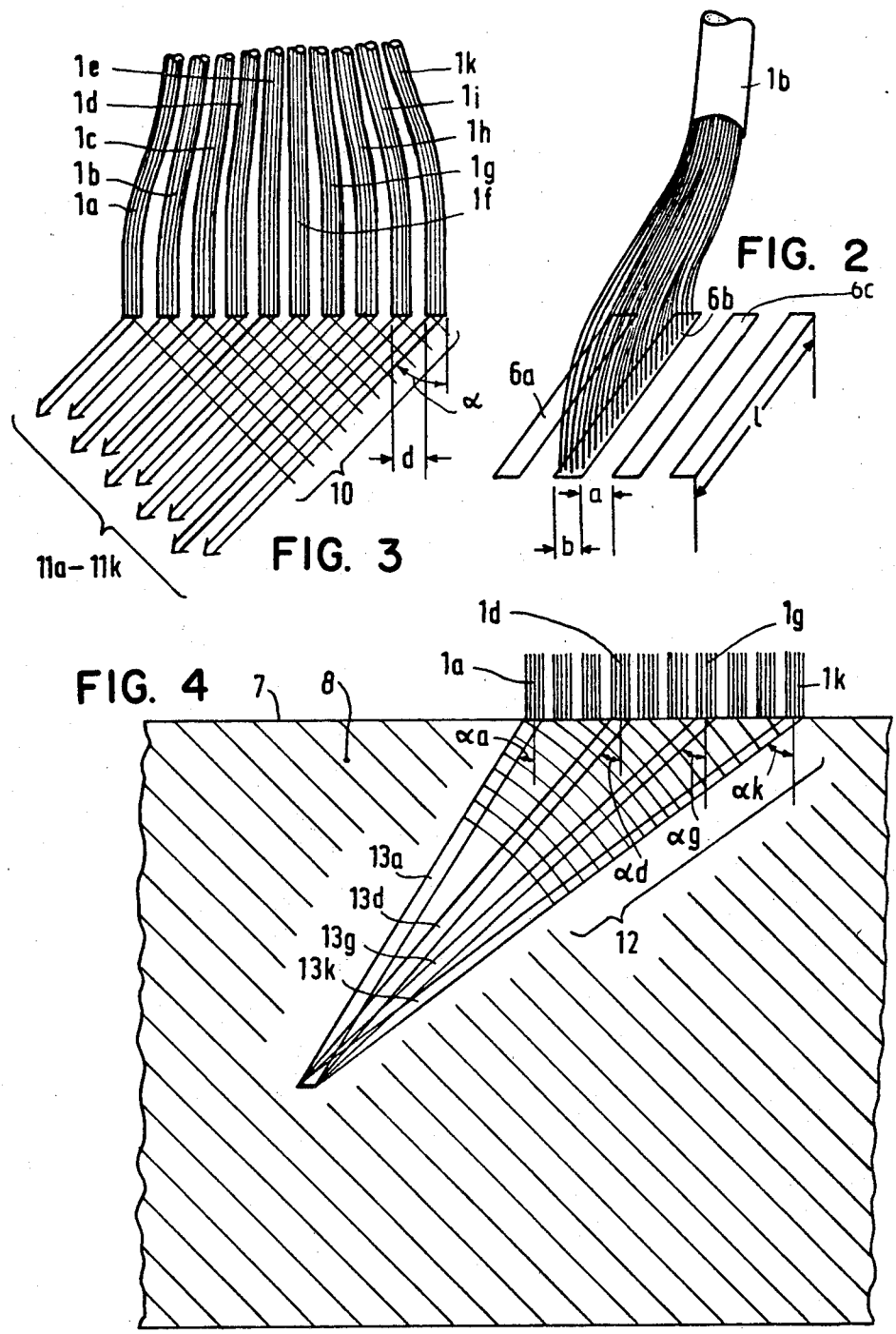

APPARATUS FOR PRODUCING ULTRASONIC WAVES IN A WORKPIECE

BRIEF SUMMARY OF THE INVENTION

This invention relates to an apparatus for producing in light absorbing workpieces ultrasonic waves with predeterminable direction of propagation and waveform for use in the nondestructive testing of materials, the ultrasonic waves being induced in the workpiece by subjecting surface zones having predetermined geometric shape to laser pulse illumination or thermal loading in predetermined sequence.

It is known to produce sound waves by means of laser pulses as described, for example, in "Ultrasonic Testing of Materials" by J. & H. Krautkramer (book), 2nd edition, Springer Verlag, New York, N.Y. (1977), pages 151 to 154. The illuminated and light absorbing surface portion of a workpiece is momentarily subjected to intensive heating by pulse energy from a laser. This thermal but localized application of energy results initially in a locally confined thermal expansion of the material, whereby a sonic wave in the form of a burst is produced as a result of the elastic properties of the workpiece material. The frequency spectrum of the ultrasonic wave depends upon the duration of the laser pulse and the pulse sequence. The direction of propagation of the sonic wave is generally perpendicular to the illuminated surface of the workpiece and is independent of the angle of incidence of the laser beam. If the ultrasonic wave is to be propagated in a direction deviating from perpendicular to the workpiece surface, then the surface of the workpiece must be illuminated in a zone-by-zone manner by known methods with a time delay from zone to zone. Using suitable values for the time delay, predetermined directions of sound propagation can be produced as a result of the interference of fundamental waves in accordance with Huygens' principle. Depending upon the zone pattern illuminated, it is possible to obtain directional ultrasonic waves with nearly plane wavefronts, i.e. a parallel ultrasonic beam, or directional ultrasonic waves having curved wavefronts for focusing the beam of sound waves. Cylindrically curved waterfronts produce a line focus of the ultrasonic beam and spherically curved waterfronts cause the ultrasonic beam to come to a focus at a point. Methods for achieving these types of ultrasonic beams by laser stimulation are disclosed in U.S. Pat. No. 4,144,767 issued to W. Kaule et al, entitled "Method and Apparatus for Producing Pulse-Shaped Acoustic Waves on a Workpiece Surface" dated Mar. 20, 1979 and in U.S. Pat. No. 4,169,662 issued to W. Kaule et al entitled "Method and Apparatus for Producing Acoustic Waves by Laser Pulses" dated Oct. 2, 1979. In these prior art arrangements individual zones are illuminated by a laser in accordance with a specific time sequence. However, these prior arrangements are afflicted with several shortcomings.

A laser source is required for each zone to be excited. This is technially complex and expensive. These lasers have to be pulsed sequentially with predetermined time delays, the orders of magnitude of the time delays required from laser to laser being in the range from 10 ns to 100 ns. However, when pulsing lasers, statistical time fluctuations of the same order of magnitude occur between the trigger pulse and the laser light pulse (jitter errors). If only one laser is used as shown in U.S. Pat. No. 4,169,662 focusing is possible only on one point along a perpendicular axis to the surface. Additionally, a considerable amount of laser light is lost on account of the zone mask required in these prior art arrangements.

A principal object of this invention is to provide an arrangement for causing a sound wave beam to be propagated in a workpiece at a predetermined direction and, if desired, come to a focus using just one laser and without the need for a zone mask or any similar light attenuating means.

Further objects and advantages of the present invention will become more clearly apparent from the following description when read in conjunction with the accompanying drawings.

BRIEF DESCRIPTION OF THE DRAWINGS

FIG. 2 depicts the transmit ends of the optical fiber bundles fanned out for transmitting energy to surface zones;

FIG. 3 is an illustration showing the ends of the optical fiber bundles and illustrates transmission of waves at an angle;

FIG. 4 is an illustrative sketch for explaining focusing of sonic waves, and

DETAILED DESCRIPTION OF THE INVENTION

Figure 1:
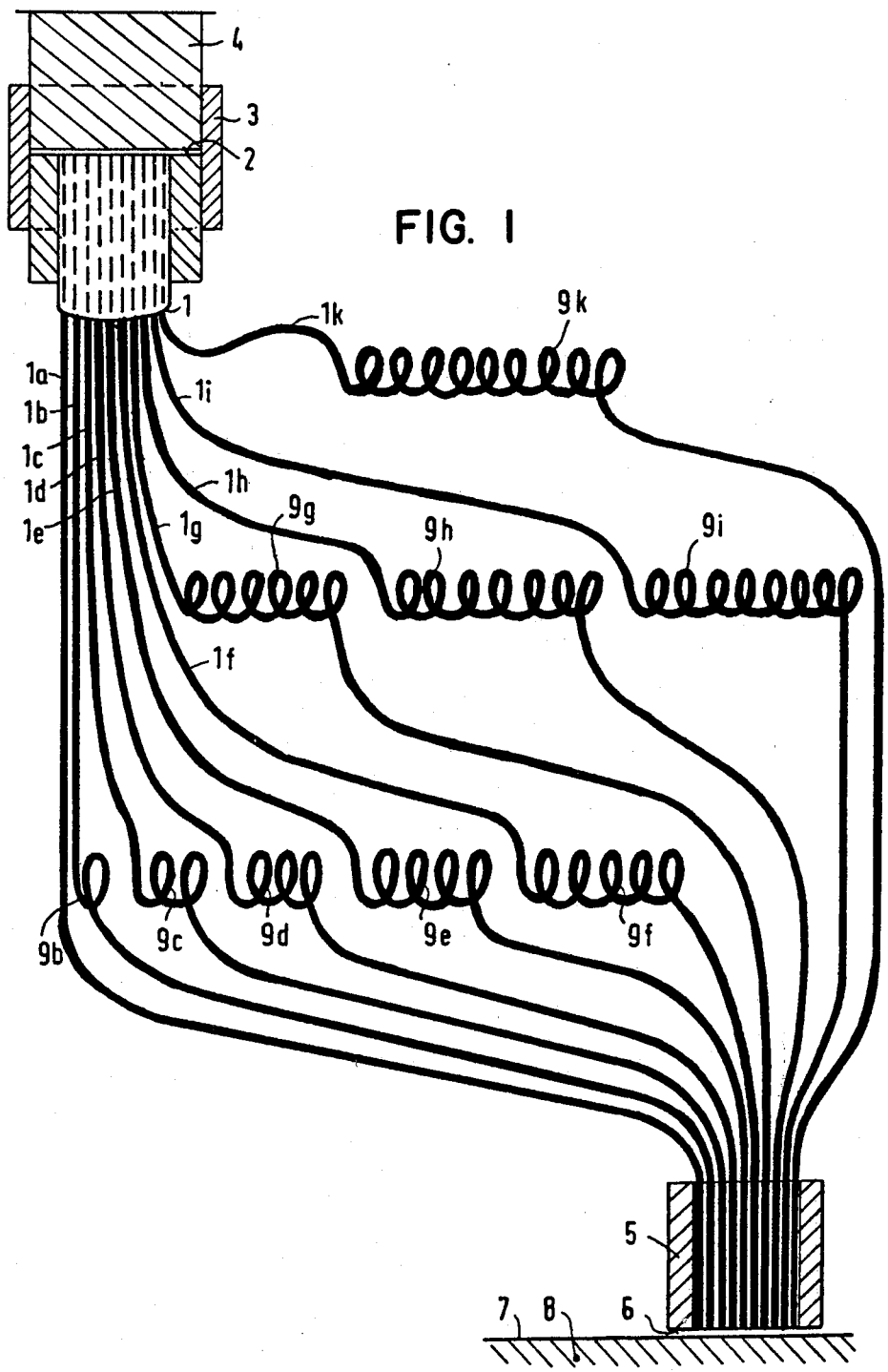
FIG. 1 is a view showing a typical embodiment of the invention.

In a preferred embodiment shown in FIG. 1, an optical fiber cable 1 comprising at least as many fiber bundles 1a, 1b, 1c to 1k as there are workpiece surface zones to be energized with laser light is coupled optically to a laser 4 by means known in the art, for instance a plug-in coupling 3. The light entry surface 2 of the fiber cable is ground flat. The bundles 1a, 1b, 1c through 1k terminate at a common end surface 6 of a probe head 5. In addition, as best seen in FIG. 2, the fiber strand ends of each bundle, as illustrated for bundle 1b, are fanned out and held in place by being embedded in plastic material within the probe head 5. The respective fanned out bundle ends, bundles 1a through 1k, are laterally spaced from one another by a predetermined distance designated by letter a, see FIG. 2. The end face 6, containing the ends of the fiber bundles, is ground flat or otherwise rendered smooth. The fiber ends of each bundle 1a through 1k are fanned out at the respective bundle output end 6a through 1k along a length L, see FIG. 2, as determined by the length of the respective surface zone.

Referring more specifically to FIG. 2, each workpiece surface zone has a width b and length L. The lateral distance between two neighboring zones is denoted with a. As shown in this example, responsive to the energizing of these bundles parallel, non-focussed sonic waves with plane wavefronts are produced in these straight (linear) strip shaped surface zone. Wavefronts occurring as a result of interference in accordance with Huygens' principle are denoted by reference numeral 10, FIG. 3, and the perpendiculars to these wavefronts, i.e. the direction of sound propagation, are denoted by references 11a to 11k. The probe head 5 constructed in this manner can be moved manually or automatically over the workpiece surface 7 as a transmission probe in a manner as is conventional when testing workpieces by means of ultrasonic energy, however in the present invention without the need for physical contact between the probe head and the workpiece surface, thus avoiding the requirement for a couplant or coupling medium between the probe frontal surface and the workpiece and eliminating, moreover, the mechanical abrasion of the probe's frontal surface normally experienced with contact testing.

The configuration and the distances between the end faces 6a–6k of the fiber bundles are governed by the laws of diffraction. If, in accordance with Huygens' principle, neighboring surface zones are energized sequentially with appropriate time delays, the wave propagation will have preferential direction on account of the interference of the fundamental waves. If only the first-order interference is considered then the angle of propagation of the waves is given by:

$$\sin\alpha = \frac{cS \cdot \Delta T}{d}$$

wherein d is the distance between the centers of wave transmission, in this case the center-to-center distance $d = 2 \cdot b/2 + a = a + b$ in FIG. 2; $\alpha$ is the angle of sonic wave propagation measured with respect to a perpendicular axis intersecting the optically energized surface 7 of the workpiece 8; cS is the speed of propagation of the sonic wave produced and $\Delta T$ equals the delay time with which the zones are energized in sequence, one after the other. This time delay is then:

$$\Delta T = \frac{d \cdot \sin\alpha}{cS}.$$

If the wave train illumination to which the workpiece surface 7 is subjected is of sufficiently long duration and, hence, capable of producing interference, the resulting diffraction patterns are the ones known from the optical grating. There is no ambiguity if the laser pulses used are of short duration and non-periodic within the range of the sonic frequencies.

If, as an example, it is desired to induce a sonic wave in a material having a sound velocity of cS=5945 m/s at an angle $\alpha = 30°$, and if the center-to-center distance d=a+b=0.2 mm (zone width b=0.1 mm and lateral spacing between neighboring zones a=0.1 mm), the resulting time delay from zone to zone is:

$$T = \frac{0.2 \text{ mm} \cdot \sin 30°}{5,945,000 \text{ mm/s}} = 16.82 \text{ ns}$$

If, in the above example, an optical fiber is selected having a signal transit time of 4.6 ns/m, corresponding to a speed of light propagation in the optical fiber $cL = 2.174 \cdot 10^8$ m/s, then the individual bundles must be lenghtened incrementally from zone to zone by:

$$\Delta L = \Delta T \cdot cL = 16.82 \cdot 10^{-9} s \cdot 2.174 \cdot 10^8 \text{ m/s} = 3.657 \text{ m}.$$

The following bundle lengths would be applicable:
Length of bundle:
1a = 5.000 m
1b = 8.657 m
1c = 12.314 m
1d = 15.971 m
1e = 19.628 m
1f = 23.285 m
1g = 26.942 m
1h = 30.599 m
1i = 34.256 m
1k = 37.913 m The individual bundles 1a through 1k can be wound on one or more spools 9b to 9k as shown in FIG. 1.

If the center-to-center distances d between the zones or the time delays are not made equal, line focusing can be obtained. FIG. 4 shows the angles $\alpha a$ through $\alpha k$ for the condition of equidistant center-to-center distances between the zones, the sound beams being denoted by reference 13 and the cyclindrically curved wavefronts by reference 12. For the case of line focusing the zones are in the form of linear strips.

The delay times are selected in accordance with the equation:

$$\Delta T_\nu = \frac{d \cdot \sin\alpha_\nu}{c} ; \nu = a \text{ to } k$$

In FIG. 4, for the sake of clarity, only four of the ten sonic beams are shown.

Of course, the invention is not restricted to the specific embodiments described. It will readily be apparent that various modifications can be made without further inventive effort, particularly in respect of the configuration of the zones and the required time delays for producing specific focusing. If, for example, the zonal strips are curved circularly, spherical wavefronts are produced, the sonic beams coming to focus at a point within the workpiece 8.

Figure 5:
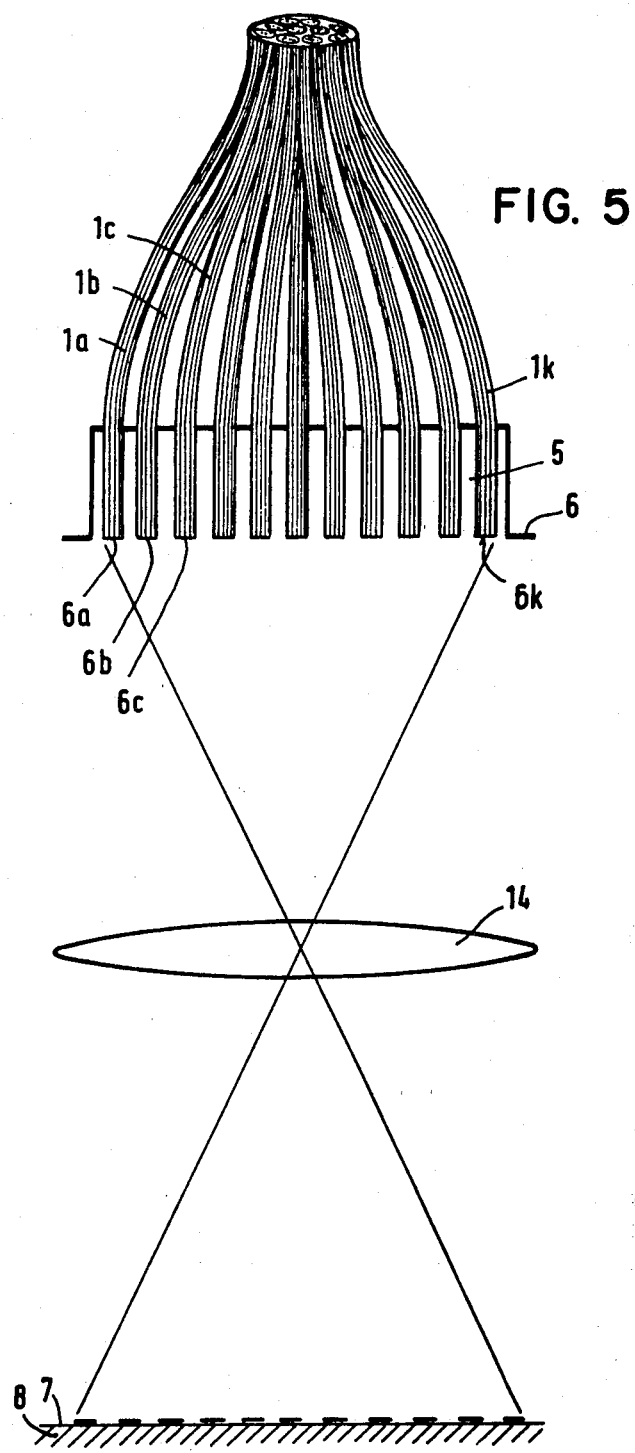
FIG. 5 is an illustration of an embodiment for contact-free optical coupling of the laser energy including optical imaging means.

If it is desired that the probe head 5 induce the sonic waves in the workpiece free of physical contact over a relatively larger gap, i.e. a gap has to be bridged between the end face 6 of the probe head 5 and the surface 7 of the workpiece 8, then an optical imaging system 14, FIG. 5, can be provided between the probe head 5 and the workpiece surface 7, thus producing a contour-sharp image of the zone pattern of the head end face 6 on the workpiece surface 7.

What is claimed is:

1. An apparatus for producing in a light absorbing workpiece ultrasonic waves having predetermined direction of propagation and wave-form, the ultrasonic waves being induced in the workpiece by subjecting spaced surface zones having predetermined geometric shapes to laser pulse illumination in predetermined time sequence comprising:

an optical fiber cable comprising a plurality of fiber bundles, each bundle having a plurality of fibers, said bundles having respective light input ends disposed at a common input surface for being coupled to a laser for receiving light energy from such laser at said input surface, and having respective light output ends disposed at a common output surface of a probe head for causing said surface zones to be illuminated with said light energy when said output surface is disposed opposite said surface zones;

the output end of each of said bundles disposed in said probe head having its fibers fanned out at said output surface in accordance with the predetermined geometric shape of a respective zone which said bundle is to illuminate, and said respective output ends of said bundles being spaced from one another along said output surface commensurate with the spacing of said zones, and means causing said fiber bundles to have different optical path lengths to provide predetermined time delays for the laser light exiting from said respective fiber bundles at said output surface when said bundles are energized simultaneously at said input surface.

2. An apparatus as set forth in claim 1, said means causing said fiber bundles to have different optical path lengths comprising causing each of said bundles to have a different length.

3. An apparatus as set forth in claim 1 or 2, said ends of said respective bundles being fanned out to exhibit the geometric shape of linear strips corresponding to a predetermined strip zonal pattern of the workpiece surface.

4. An apparatus as set forth in claim 3 and optical imaging means disposed between said output surface and the workpiece surface.

* * * * *